US007497575B2

(12) United States Patent  
Huang et al.

(10) Patent No.: US 7,497,575 B2  
(45) Date of Patent: Mar. 3, 2009

(54) GAUSSIAN FITTING ON MEAN CURVATURE MAPS OF PARAMETERIZATION OF CORNEAL ECTATIC DISEASES

(75) Inventors: David Huang, South Pasadena, CA (US); Maolong Tang, San Gabriel, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/743,136

(22) Filed: May 1, 2007

(65) Prior Publication Data

US 2007/0291228 A1 Dec. 20, 2007

Related U.S. Application Data

(60) Provisional application No. 60/796,916, filed on May 1, 2006.

(51) Int. Cl.
*A61B 3/14* (2006.01)
*A61B 3/10* (2006.01)

(52) U.S. Cl. .................................. 351/206; 351/212
(58) Field of Classification Search .......... 351/200–246
See application file for complete search history.

(56) References Cited

U.S. PATENT DOCUMENTS 5,406,074 A * 4/1995 Grisell ....................... 250/221
6,338,559 B1 * 1/2002 Williams et al. ............ 351/212

* cited by examiner

*Primary Examiner*—Mohammed Hasan
(74) *Attorney, Agent, or Firm*—Hogan & Hartson LLP (57) ABSTRACT

The present invention discloses a method for characterizing ectatic diseases of the cornea by computing a mean curvature map of the anterior or posterior surfaces of the cornea and fitting the map to a Gaussian function to characterize the surface features of the map. Exemplary ectatic disease that may be characterized include keratoconus and pellucid marginal degeneration. Also disclosed are a system for diagnosing ectatic disease of the cornea and a computer readable medium encoding the method thereof.

20 Claims, 12 Drawing Sheets

GAUSSIAN FITTING ON MEAN CURVATURE MAPS OF PARAMETERIZATION OF CORNEAL ECTATIC DISEASES

CROSS-REFERENCE TO RELATED APPLICATIONS

This application claims an invention which was disclosed in Provisional Application No. 60/796,916 filed on May 1, 2006. The benefit under 35 USC §119(e) of the United States provisional application 5 is hereby claimed. The above priority application is hereby incorporated herein by reference.

FIELD OF THE INVENTION

The invention pertains to the field of ophthalmology. More particularly, the invention pertains to characterization of cornea shape and diagnosis of ectatic disease of the cornea.

BACKGROUND OF THE INVENTION

Keratoconus is a degenerative non-inflammatory disorder of the eye in which structural changes within the cornea cause it to thin and change to a more conical shape than its normal gradual curve. Keratoconus can cause substantial distortion of vision, with multiple images, streaking and sensitivity to light all often reported by the patient. Keratoconus is the most common dystrophy of the cornea, affecting around one person in a thousand, and it seems to occur in all ethnic groups worldwide, although for some groups the prevalence of keratoconus is greater than others. It is typically diagnosed in the patient's adolescent years and attains its most severe state in the twenties and thirties.

Keratoconus is a little-understood disease with an uncertain cause, and its progression following diagnosis is unpredictable. If afflicting both eyes, the deterioration in vision can affect the patient's ability to drive a car or read normal print. It does not however lead to blindness, and in most cases, corrective lenses are effective enough to allow the patient to continue to drive legally and likewise function normally. Further progression of the disease may lead to a need for surgery. Despite its uncertainties, keratoconus can be successfully managed with a variety of clinical and surgical techniques, and often with little or no impairment to the patient's quality of life.

Pellucid marginal degeneration (PMD)—is a rare condition whereby the lower cornea becomes thinner and the optic surface of the cornea becomes irregular and the vision becomes blurry. The resulting shape of the cornea is similar to a pregnant belly whereby the lower portion of the cornea protruding forward. PMD is often misdiagnosed as Keratoconus, although similar, the resulting cornea shape can be quite different. PMD often has cornea sizes similar to that of a regular eye but a very steep curve in the bottom of the cornea. PMD has been observed in families giving it an inherited trait and on occasion it has been observed unilaterally in one eye only. Typically it is bilateral affecting both eyes.

It is important to rule out both these conditions in LASIK candidates to avoid post-LASIK keratectasia which represents an iatrogenic exacerbation of the disease. Corneal topography is essential for the diagnosis of form fruste (preclinical) keratoconus where the patient may not recognize the symptoms, visual acuity may be good, and the cornea may appear normal on slit-lamp biomicroscopy.

Placido-ring corneal topography is usually represented as axial and tangential power maps. The recognition of keratoconus and PMD on these maps is not easy because there is no simple characteristic pattern. Early stages of the disease are especially difficult to distinguish from normal variations. The topography of central keratoconus shows central steepening which may be difficult to distinguish from the natural asphericity of the cornea. An off-center cone may produce an asymmetric bowtie, skewed bowtie, J, or U shaped patterns. PMD typically presents a "butterfly" pattern. As a result, diagnostic systems on the basis of the axial and tangential maps must employ multiple indices that extract features of these different patterns.

Therefore, there still exists a need for a better method of detecting and diagnosing ectatic diseases of the cornea.

SUMMARY OF THE INVENTION

In one aspect, the present invention provides a method for characterizing corneal anterior and posterior surfaces by utilizing mean curvature maps of the cornea and fitting the map to a mathematical function having a cone-like shape.

Mean curvature is an alternative representation of the corneal surface that may simplify the recognition of keratoconus and PMD. Mean curvature is computed at each point on a surface by averaging the curvature along two orthogonal principal directions. It is equivalent to the inverse of the radius of the best-fit local sphere. An astigmatic surface appears relatively uniform (no bowtie pattern) on the mean curvature map because the curvature is averaged along two perpendicular directions. Ectasia produces a local increase in mean curvature that is not affected by astigmatism or location relative to the center of the cornea. This feature may make it easier to pick out the "cone" in keratoconus.

Mean curvature can be converted to dioptric units using a model of the cornea that includes the refractive index transitions at the air, cornea, and aqueous interfaces. While the inventors do not wish to be bound by any particular theory or explanatory narrative, one may think of dioptric mean curvature as representing the refractive power of a spherical cornea with a mean curvature equal to the local surface. For comparison, the axial power represents the corneal refractive power of a sphere with a radial slope equal to the local surface. The tangential power represents the corneal refractive power of a sphere with a radial curvature equal to the local surface. Dioptric mean curvature is a measure of spherical equivalent power and does not contain information on astigmatism. The axial power is a paraxial approximation to a refractive power calculation according to Snell's law. Both mean curvature and tangential power are on the basis of curvature and are more sensitive to localized shape changes. Mean curvature mapping is potentially a better method for detecting corneal ectatic conditions.

In another aspect, the present invention provides a system for diagnosing ectatic conditions in cornea.

In another aspect, the present invention also provides a computer readable medium encoding a method according to embodiments of the present invention.

Other aspects and advantages of the invention will be apparent from the following description and the appended claims.

DETAILED DESCRIPTION

The present invention will now be described in detail by referring to specific embodiments as illustrated in the accompanying figures.

As described above, detection and recognition of ectatic diseases in the cornea are difficult using conventional methods of corneal topography analysis. Accordingly, it is one object of the present invention to provide an accurate and precise method for the detection and recognition of different ectatic diseases.

In one aspect, the present invention provides a method for analyzing cornea cone characteristics comprising the steps of a) computing a map of the cornea; b) fitting the map to a mathematical function having a cone-like shape; and c) determining the cone's location based on the fitting.

Corneal maps used in a method of the present invention may be obtained from Placido ring-based corneal topography, optical coherence tomography, slit-scanning pachymetry, ultrasound imaging or any other suitable measuring means commonly known in the art. The map is preferably of the anterior surface of the cornea. The current invention also applies to other types of maps such as the posterior surface of the cornea and the corneal thickness (pachymetry). Pachymetry measurements are known in the art. References [4]-[6] provides further information about pachymetry, the contents of which are incorporated herein in their entirety. Preferably, the map is captured in digital format or in a format that can be easily converted to a digital format.

In one embodiment, the surface map comprises a raw corneal topography data in the form of an axial radial matrix or elevation matrix. In another embodiment, the surface map is a mean curvature map. The mean curvature map may be obtained by first converting the raw corneal topography map into an elevation map. The elevation map may then be used to compute a mean curvature map.

Preferably, the elevation map is computed by the arc-step algorithm (see reference [1], the content of which is incorporated herein in its entirety), but other suitable algorithm commonly known in the art may also be used.

Preferably, the mean curvature map is computed by the algorithm described in reference [2], the content of which is incorporated herein in its entirety, but other suitable algorithms commonly known in the art may also be used.

In another embodiment, the corneal map is a pachymetry map.

Figure 1:
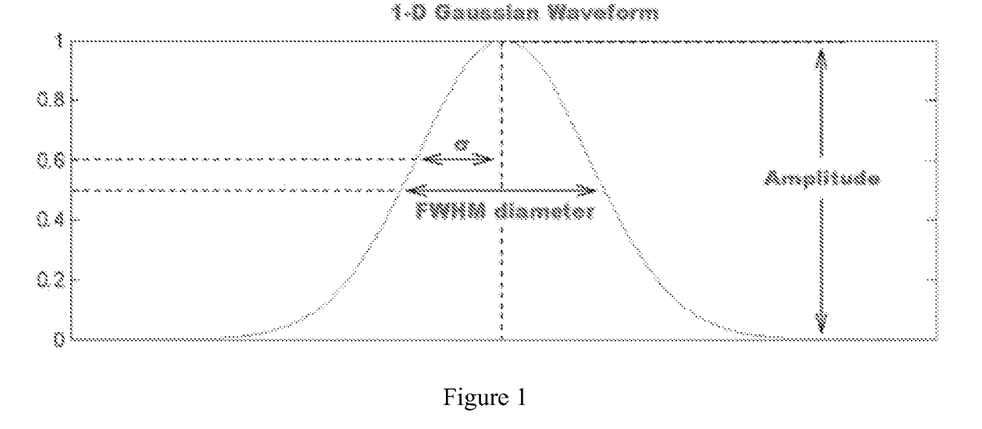
FIG. 1 shows an one-dimensional Gaussian waveform.

For fitting the corneal map to a mathematical function having a cone-like function, a variety mathematical functions may be utilized. In one embodiment, Gaussian functions are preferably used. FIG. 1 shows a typical Gaussian function waveform. A waveform may be described by several parameters including its amplitude and width. For the purpose of the present invention, a Gaussian waveform is used to model the surface curvature of a cornea. Thus, the relevant parameters are the height of the waveform and the width of the waveform, as shown in FIG. 1.

In one further embodiment, the Gaussian function is a radically symmetric two-dimensional Gaussian function. In one exemplary embodiment, each surface map is fitted to the following Gaussian function:

$$f(x, y) = A \exp\left[-\frac{(x-x_0)^2 + (y-y_0)^2}{2\sigma^2}\right]$$

where A describes the amplitude or height of the cone, $\sigma$ is the standard deviation of the fitted Gaussian function that characterize the width of the cone, $(x_0, y_0)$ specifies the location of cone peak in Cartesian coordinates.

In other embodiments, the Gaussian function may have different horizontal and vertical diameters. In yet other embodiments, functional forms containing still further parameters may be used.

Using similar fitting procedures as described above, other cone-like functional forms that may be used include, but not limited to $4^{th}$-order 0-period Zernike polynomial $Z_4^0$, and probability density functions of the exponential family like Alpha, Rayleigh, and Cauchy.

In some other embodiments, a method of the present invention may further comprise a step of smoothing the surface map with a moving average window. Preferably, the smoothing moving average window may have a size in the range of from about 0.02 mm by 0.02 mm to about 2 mm by 2 mm. More preferably, the window size may be from about 0.1 mm by 0.1mm to about 1.0 mm by 1.0 mm. In one exemplary embodiment, the window size is about 0.6 mm by 0.6 mm.

The cone's location may be determined by identifying the maximum mean curvature value from the smoothed map.

In another aspect, the present invention provides a method for detecting ectatic diseases of a cornea. When a method of the present invention as described above is applied to the analysis of a cornea surface map of a subject, a diagnosis of corneal disease may be obtained. Exemplary corneal diseases that may be applicable include, but not limited to keratoconus, pellucid marginal degeneration, and other corneal ectatic diseases. Methods of the present invention are particularly useful for differentiating between keratoconus and pellucid marginal degeneration.

Exemplary methods of the present invention for detecting ectatic diseases generally comprises the steps of: a) providing a mean curvature map of the cornea; b) fitting the map to a Gaussian function; c) determining the location of the cornea's cone based on the fitting; and d) comparing the amplitude of the cone to the normal range of variation of healthy eyes, wherein if the amplitude of the cone deviates from the reference location by a pre-determined amount, a diseased state is detected. The location of the cone provide further information on whether the disease is likely to be keratoconus or PMD. The cone location for an eye with PMD is typically more inferior than that of an eye with keratoconus.

In another exemplary method, the inverse normalized pachymetry map is used instead of the mean curvature map. The inverse normalized pachymetry map is the pachymetry map of the average normal eye divided by the pachymetry map of the eye under examination.

Methods of the present invention may be implemented in an integrated system that is full automated or in a system assembled from off-the-shelf parts that require some manual intervention. In general, a system according to the present invention may comprise the components of a corneal topography measuring device capable of measuring and generating a corneal topography either in a digital format or in a format capable of being digitized, and a processing unit. Corneal topography measuring device may include, but not limited to Placido-ring corneal topography, slit-scan corneal topography, Scheimpflug-camera corneal topography, raster photogrammetry, optical coherence tomography, or any other suitable corneal measuring devices known in the art. The processing unit may be a personal computer workstation, an embedded processor, or any other suitable data processing device commonly known in the art.

In addition to being implemented in a system, methods of the present invention may also be provided in the form of a software encoded on a computer readable media for distribution to end users. Exemplary computer readable media may include, but not limited to floppy disks, CD-ROMs, DVD, hard drive disks, flash memory cards, or any other computer readable media commonly known in the art.

To further illustrate the present invention, the following specific examples are provided

EXAMPLES

Material and Methods

Keratoconus and Pellucid Marginal Degeneration (PMD) cases were identified by a review of the diagnosis codes (CPT) in The Cleveland Clinic Cole Eye Institute database. The retrospective chart review was approved by the institutional review board of the Cleveland Clinic. We identified those cases that had complete clinical chart documentation of slit-lamp findings and readable files on the C-Scan corneal topography system (Technomed, Berlin, Germany). Nineteen eyes with keratoconus and eight with PMD were identified. The cases were reviewed by authors D. M. and D. H. for proper classification. The inclusion criteria were history, slit-lamp findings, and corneal topographies consistent with a diagnosis of keratoconus or PMD, no history of previous corneal surgery, and topography maps with valid data points over a central area of more than 6 mm in diameter.

The cases were divided into the keratoconus and PMD groups on the basis of the topographic and clinical appearances. The keratoconus group was further subdivided into early and advanced subgroups. The advanced keratoconus subgroup included fifteen eyes with single or multiple slit-lamp manifestations, including Munson's sign, evidence of past hydrops, Vogt's striae, Fleisher's ring, subepithelial opacity, apical thinning, and visible ectatic deformation. The remaining four keratoconic eyes without slit-lamp signs were included in the early keratoconus subgroup.

The raw corneal topography data (axial radius matrix) were exported from the topography system and used to compute maps on digital grids of 10 mm×10 mm with a uniform sampling interval of 0.02 mm. The axial maps were converted to the elevation maps using an arc-step algorithm [1]. The elevation map was then used to compute mean curvature maps using an algorithm that we have previously described [2]. Although mean curvature is poorly correlated with refractive power, we converted the curvature measurement from the natural inverse meter (1/m) units into dioptric (D) units because clinicians are more familiar with dioptric quantities in keratometry and topography. A keratometric index of 1.3375 was used for this conversion. This is the same convention that is used by the Orbscan II topography system (Bausch and Lomb, Rochester, N.Y.) to measure "keratometric mean power." We called this quantity "keratometric mean curvature." We believe "mean curvature" is less ambiguous than "mean power" since mean power can be confused with the mean of simulated keratometry (Sim-K) on two meridians. It can also be confused with the mean of axial power within a central circular area, commonly 3 or 5 mm diameter areas.

We chose to model the focal ectasia (cone) in keratoconic corneas with the radially symmetric two-dimensional Gaussian function. The function describes a cone-like surface and was previously used to describe the keratoconic elevation topography. 10 The shape of the cone on the mean curvature map also appears qualitatively similar to the Gaussian function. Each mean curvature map was fitted with a Gaussian function:

$$f(x, y) = A \exp\left[-\frac{(x - x_0)^2 + (y - y_0)^2}{2\sigma^2}\right]$$

where A describes the amplitude or height of the cone, $\sigma$ is the standard deviation of the fitted Gaussian function that characterize the width of the cone, $(x_0, y_0)$ specifies the location of cone peak in Cartesian coordinates. FIG. 1 shows a one-dimensional Gaussian function and its relative parameters.

The position $(x_0, y_0)$ of the cone peak was found by locating the maximum mean curvature value after the map was smoothed with a 0.6 mm by 0.6 mm moving average window. The center of the topographic map was aligned with the instrumental axis of the topography system, sometimes called the vertex. The cone peak positions were referenced to this corneal position. The width parameter s was found by a search algorithm that maximized the cross-correlation coefficient between the mean curvature map and the Gaussian function. We defined the cone width as the full-width-half-maximum (FWHM) diameter, which was equal to 2.35 times s. The amplitude A was the cross-correlation product between the mean curvature map and the normalized Gaussian function.

On the axial and tangential power maps, the apparent cone peak was defined as the location of the maximum value after the same smoothing. The statistics on cone parameters were derived on the basis of the Gaussian fitting of mean curvature maps from our clinical series.

In addition to real topographic data from keratoconus and PMD cases, we also used simulated corneal topography maps to test our mean curvature algorithms. The simulations started with the average corneal anterior topography, modeled as a prolate ellipsoid with an apical radius of 7.6 mm (equivalent to 44.4 diopters) and asphericity of Q=−0.26. On top of this average elevation map, we added astigmatism and cone. Astigmatism was simulated by adding the Zernike polynomial term $Z_{2,\pm2}$. The cones were added as radially symmetric Gaussian functions of 42 μm height and 3.6 mm FWHM diameter on the elevation maps. The simulated elevation maps were then used to compute axial, tangential, and mean curvature maps. The cone parameters were computed from the mean curvature maps using the same procedure applied to real topographic maps. Where appropriate, values are expressed as mean±SD.

Image processing and simulations are performed using MatLab software version 5.3 (The Mathworks, Inc, Natick, Mass.). Statistical analysis was performed using JMP software Version 4 (SAS Institute, Cary, N.C.).

Results

Figure 2:
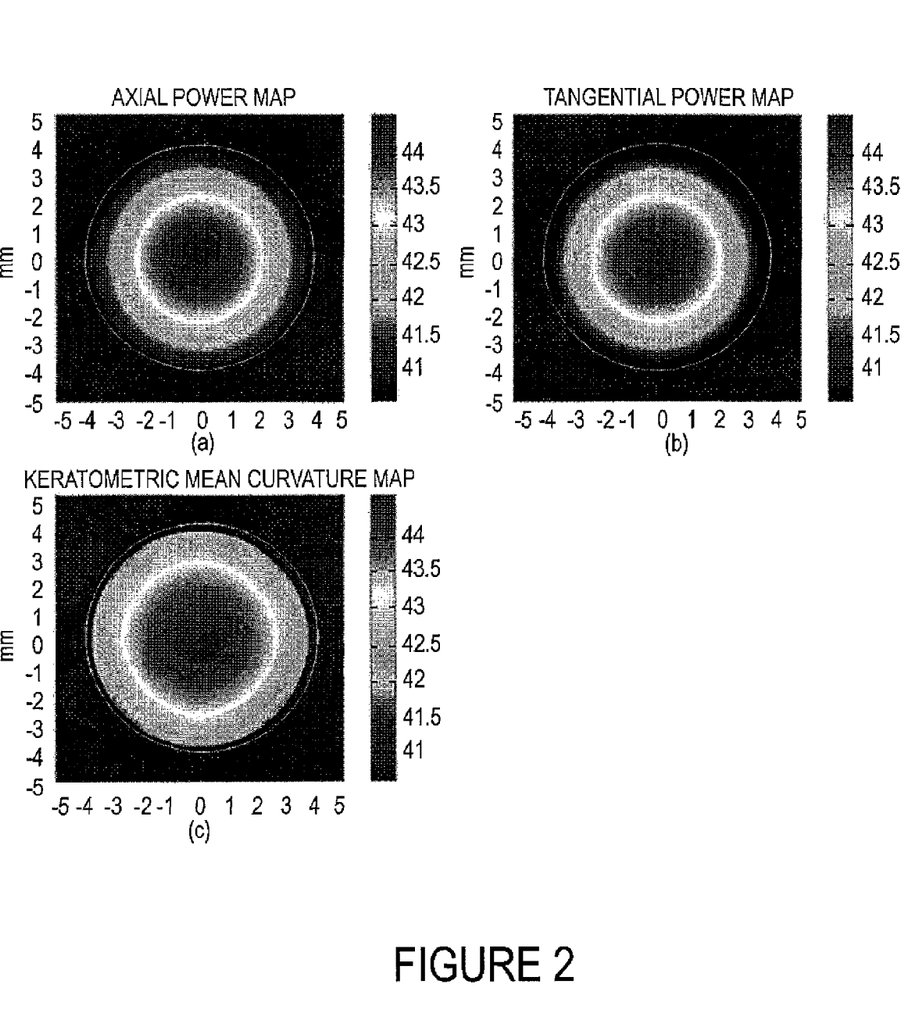
FIG. 2 shows a simulated topography of the average cornea. (a) Axial power map, (b) tangential map, (c) mean curvature map.
Figure 3:
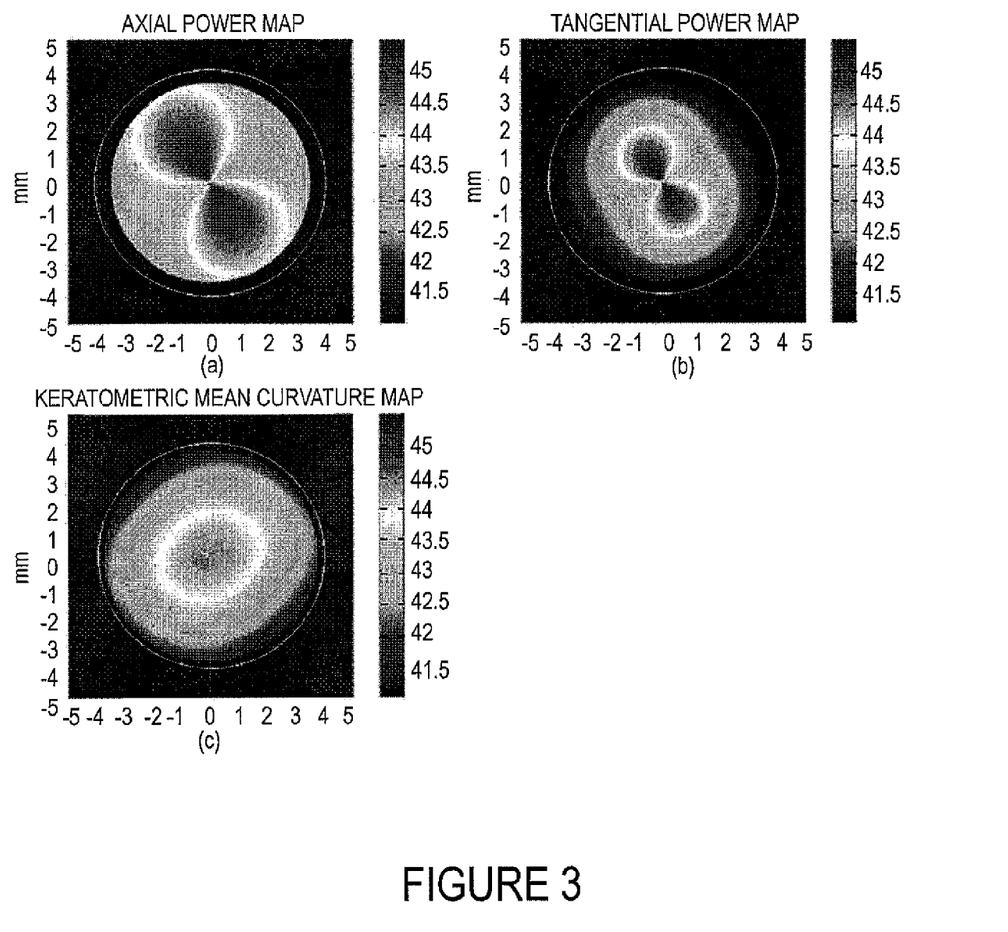
FIG. 3 shows a simulated topography of a toric cornea. The torus was modeled with 4 diopters of oblique astigmatism with a steep axis at 120 degrees. (a) Axial power map, (b) tangential map, (c) mean curvature map.

We first provided examples to illustrate the properties of mean curvature maps in relation to the more familiar axial and tangential maps. In a simulated corneal topography with average curvature and asphericity, the axial power map (FIG. 2a), the tangential map (FIG. 2b), and the mean curvature map (FIG. 2c) all had similar patterns. The prolate asphericity of the cornea made the center steeper (axial) and more convexly curved (tangential and mean curvature) than the periphery. With added astigmatism, a bowtie pattern appeared on the axial and tangential maps (FIGS. 3a and 3b). Astigmatism had a minimal effect on the mean curvature map (FIG. 3c), adding only a slight ellipticity. The ellipticity was attributable to the parabolic shape of the Zernike astigmatism formulation, which was slightly less convex towards the periphery.

Figure 4:
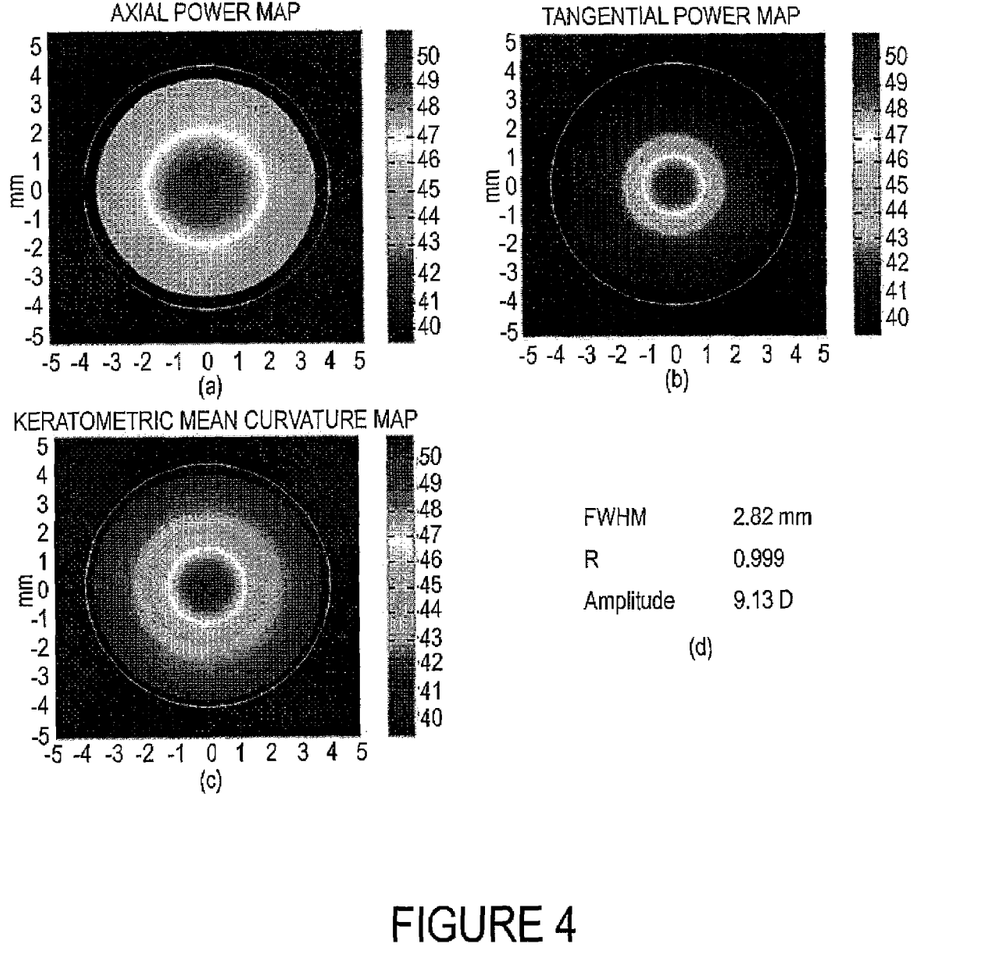
FIG. 4 shows a simulated central keratoconus. (a) Axial map, (b) tangential map, (c) mean curvature map, (d) cone parameters computed from the mean curvature map.

In the model of a cornea with a central cone, the cone appeared broader because the axial map (FIG. 4a) was on the basis of the slope (integral of curvature). The tangential and mean curvature maps (FIGS. 4b and 4c) showed the true dimension of the cone.

Figure 5:
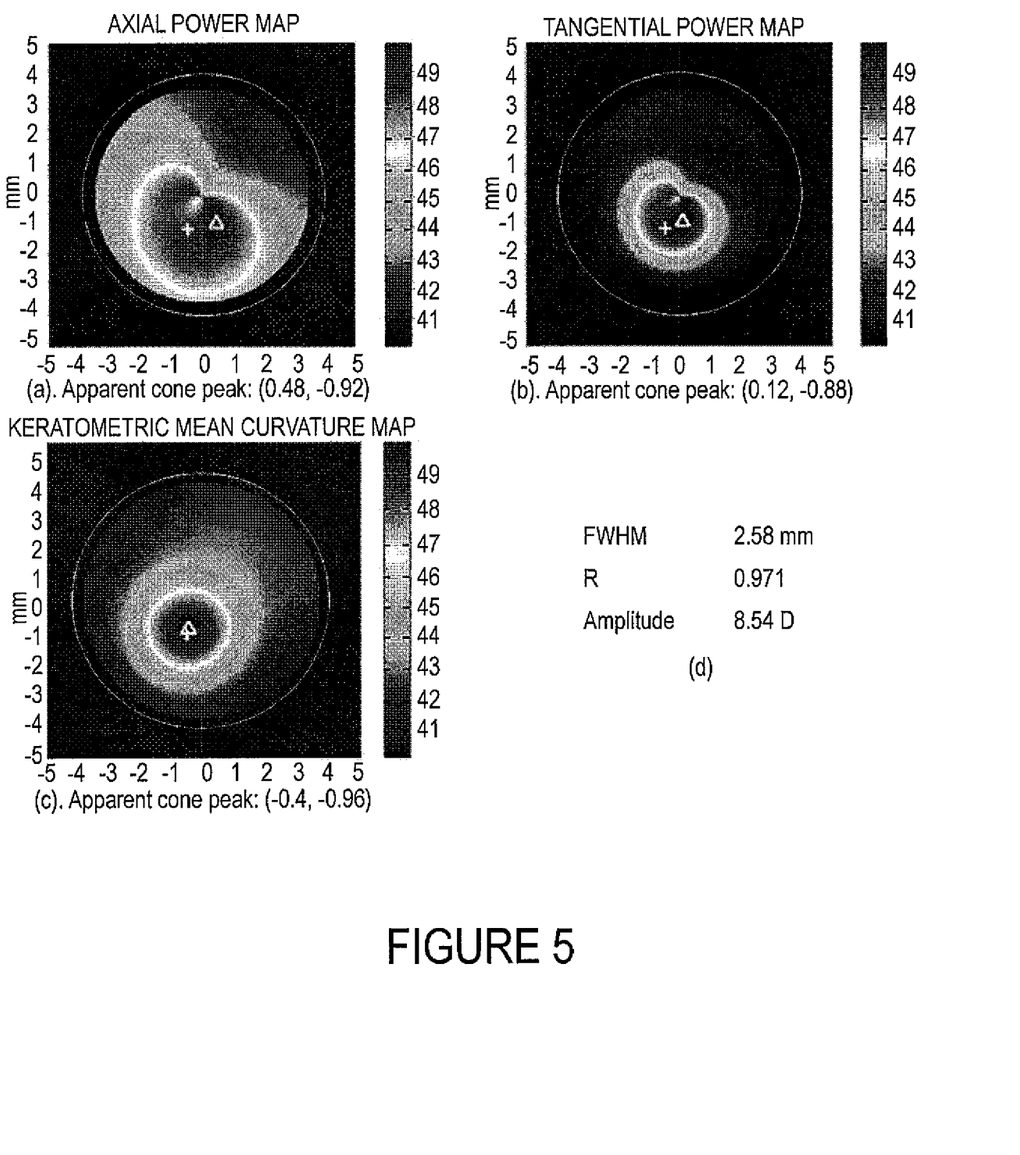
FIG. 5 shows a simulated inferior keratoconus. (a) Axial map, (b) tangential map, (c) mean curvature map, (d) cone parameters computed from the mean curvature map. The true cone peak location is marked by a cross, and the apparent peak is marked by a triangle.

Simulations of the typical keratoconic topography showed inferior displacement of the cone and coexisting astigmatism (FIG. 5). Both axial and tangential maps had asymmetric and skewed bowtie patterns typical for keratoconus (FIGS. 5a and 5b). The mean curvature map showed the true shape and peak location of the simulated cone (FIG. 5c). On the axial and tangential maps, the peak lay between the steep meridian of the astigmatism and the true cone peak location.

The simulated PMD topography showed against-the-rule astigmatism in addition to inferior steepening in a complex "butterfly" pattern (FIG. 6) with the same cone and astigmatism parameters (except axis) as in FIG. 5. The change in the astigmatism axis and inferior shift of the cone produced a qualitatively different pattern on the axial and tangential maps (FIGS. 6a and 6b). In contrast, the mean curvature map provided an undistorted display of the shape and location of cone peak (FIG. 6c).

Figure 6:
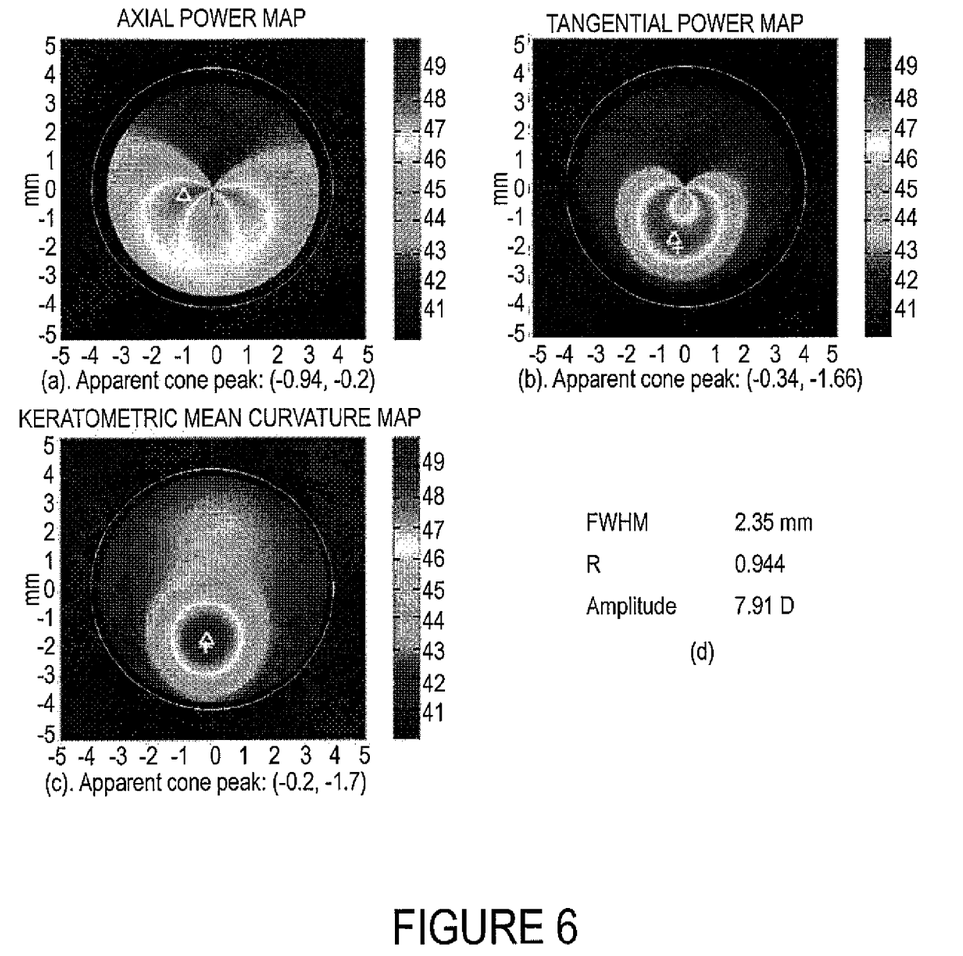
FIG. 6 shows a simulated PMD. (a) Axial map, (b) tangential map, (c) mean curvature map, (d) cone parameters computed from the mean curvature map. The true cone peak location is marked by a cross, and the apparent peak is marked by a triangle.

Cone parameters from simulated corneal topography mean curvature maps were computed for FWHMs, correlation coefficients (R), and amplitudes (FIGS. 4d, 5d, and 6d).

Comparisons of topographical maps that simulate central cones (FIG. 4d), inferior keratoconus (FIG. 5d), and PMD (FIG. 6d) reveal that the cone location has a slight effect on the apparent amplitude of the cone on mean curvature maps. Central cones appear slightly more convex (9.13 diopters) than PMD cones (7.91 diopters) because of the prolate asphericity of the cornea. However, this effect is minor. The widths of the cones on the mean curvature maps (2.35 to 2.82 mm) are narrower than the original 3.6 mm width defined in the elevation map. Overall, the simulations show that Gaussian fitting of the mean curvature map recovers the cone amplitude, width, and peak locations with minimal interference from any shift in location and change in astigmatism. Conversely, the patterns appear qualitatively different on axial and tangential maps when cone location and astigmatism were varied.

Figure 7:
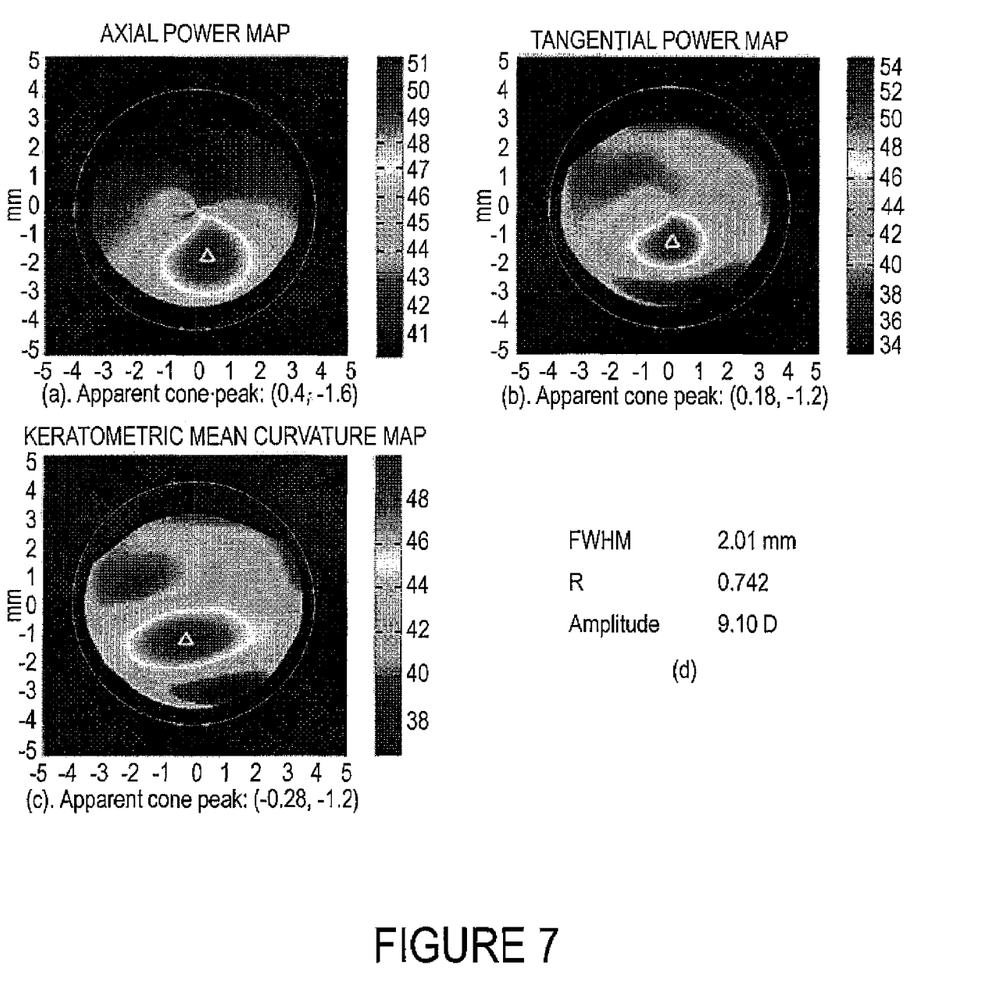
FIG. 7 shows an example of early keratoconus (right eye). (a) Axial map, (b) tangential map, (c) mean curvature map, (d) cone parameters computed from the mean curvature map. The apparent cone peak is marked by a triangle.
Figure 8:
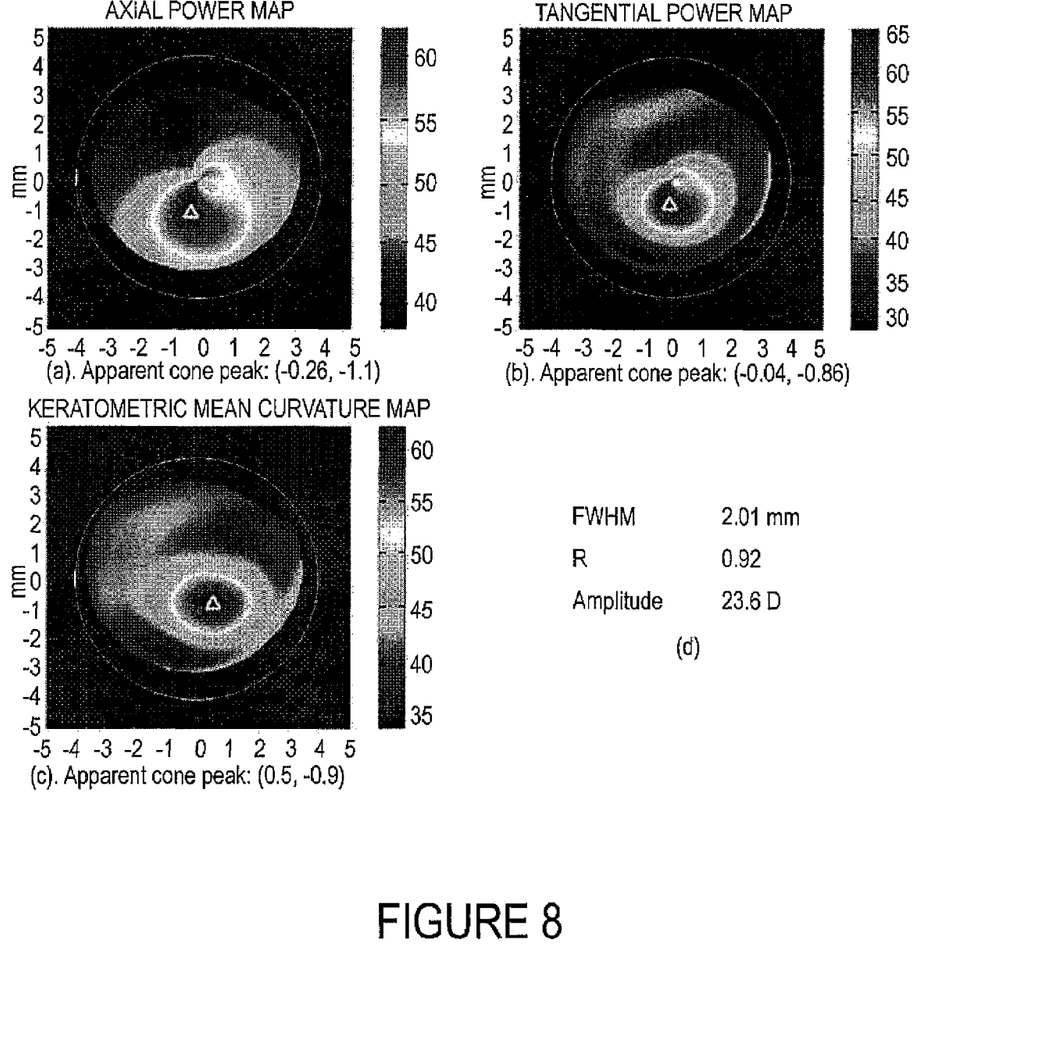
FIG. 8 shows an example of advanced keratoconus (left eye). (a) Axial map, (b) tangential map, (c) mean curvature map, (d) cone parameters computed from the mean curvature map. The apparent cone peak is marked by a triangle.
Figure 9:
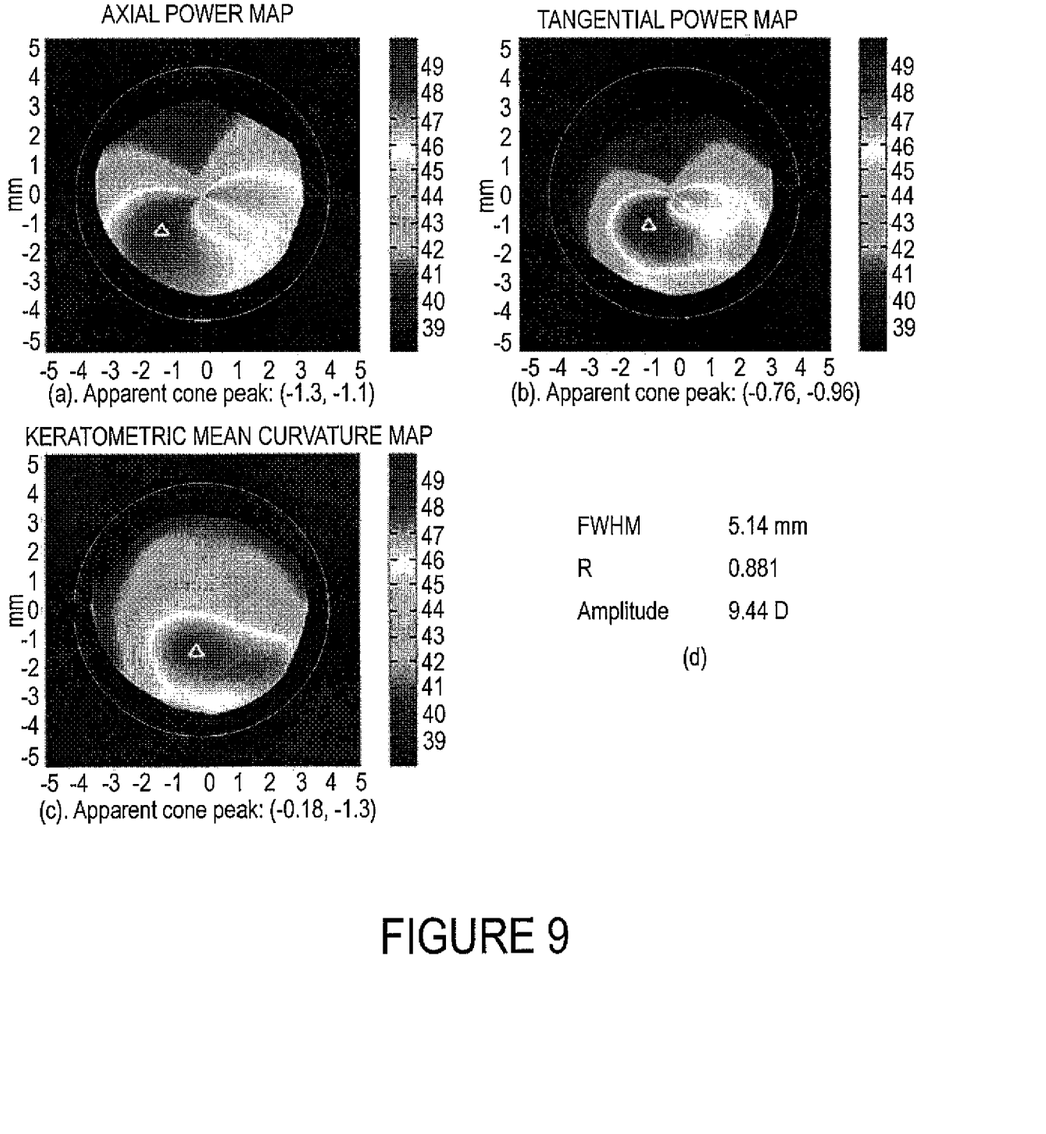
FIG. 9 shows an example of PMD (left eye). (a) Axial map, (b) tangential map, (c) mean curvature map, (d) cone parameters computed from the mean curvature map. The apparent cone peak is marked by a triangle.

The patterns of real topographies from the clinical series representing early keratoconus, advanced keratoconus, and PMD were qualitatively similar to the models shown in FIGS. 5 and 6. In both early and late keratoconic eyes, the peaks were located in the inferonasal quadrants on the axial and tangential maps (FIGS. 7a, 7b, 8a, and 8b), whereas the mean curvature maps (FIGS. 7c and 8c) located the cones inferotemporally. In PMD corneas, the axial and tangential maps had the characteristic butterfly pattern (FIGS. 9a and 9b), whereas the mean curvature maps (FIG. 9c) showed a relatively broad, inferior cone. In all three examples, the cones appeared broader horizontally on the mean curvature maps (FIGS. 7c, 8c, and 9c). This asymmetry was absent in our idealized circular cone model. Numerical cone parameters computed from the mean curvature maps are shown in FIGS. 7d, 8d, and 9d, respectively.

Figure 10:
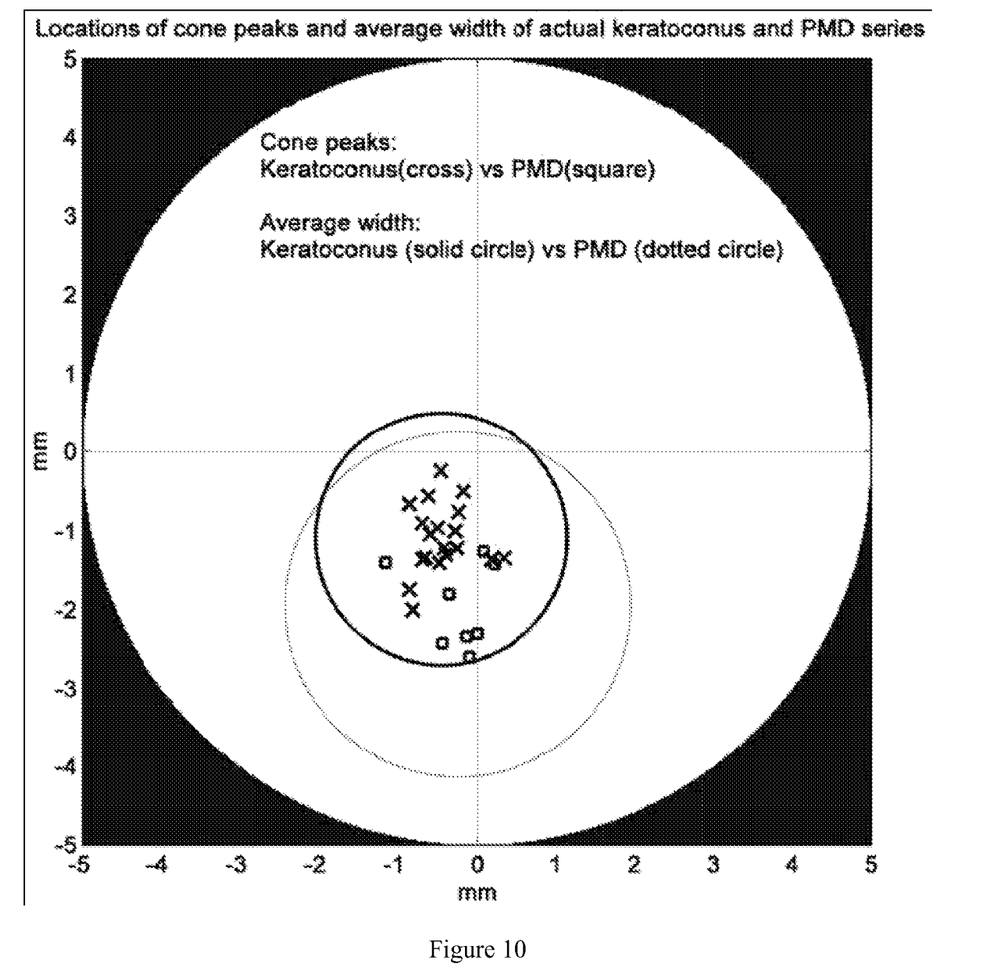
FIG. 10 shows cone peak locations on the basis of mean curvature analysis. The peak locations were plotted for keratoconus eyes (crosses) and PMD eyes (squares). Average cone diameter and location: keratoconus (solid circle) and PMD (dotted circle).

Individual cone peak locations and average cone diameters for 19 keratoconic eyes and eight PMD eyes were plotted (FIG. 10) and tabulated (Table 1). The cones in the PMD Group were located considerably more inferiorly and were lower in amplitude compared with the keratoconus group. PMD cones also tended to be broader, but this was not statistically significant. The overall average diameter of cones for combined keratoconus and PMD Groups was 3.22±1.32 mm. In both groups, the ectasia tended to occur in the inferotemporal quadrant with only a few exceptions occurring in the inferonasal quadrant. We used the cross-correlation coefficient R to measure the goodness of Gaussian fitting to the surface shape, with 1 signifying a perfect fit and 0 showing absence of correlation, The R value was 0.80 in the keratoconus group and 0.82 in the PMD Group.

Figure 11:
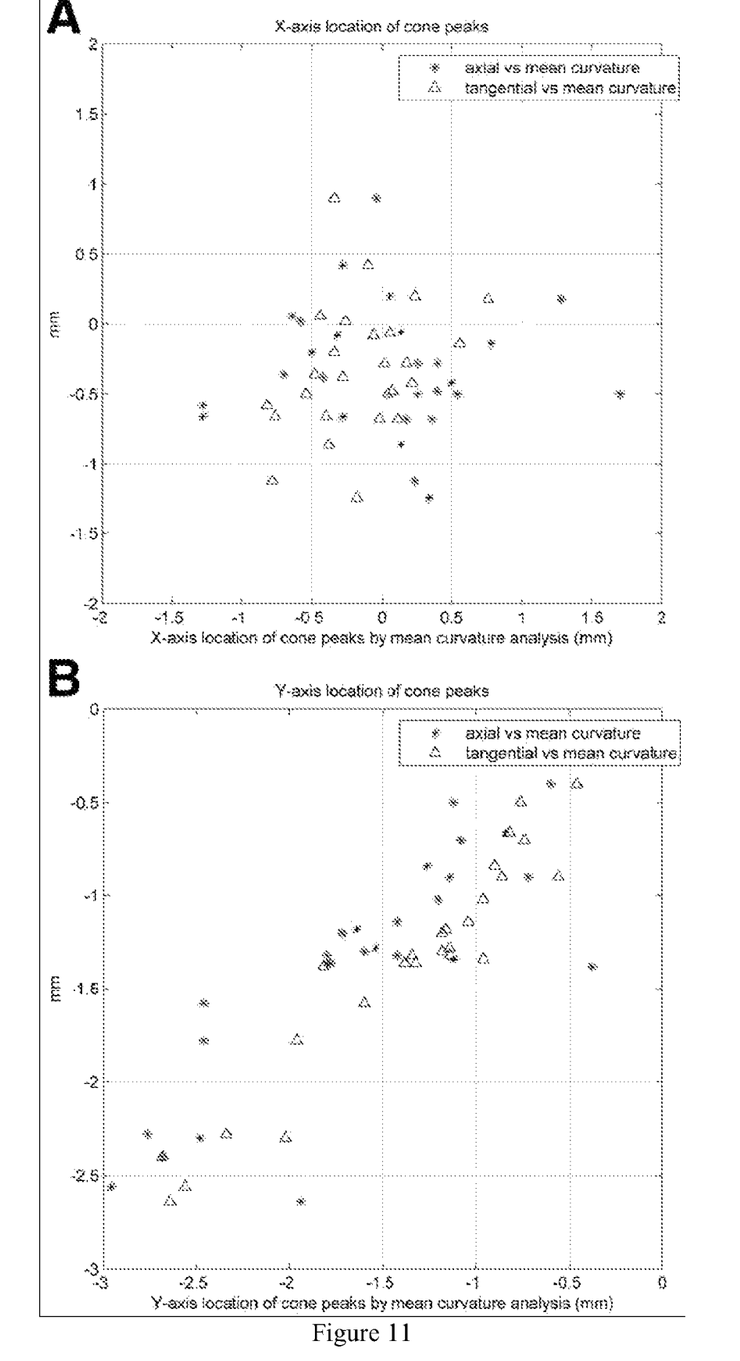
FIG. 11 shows cone peak locations in axial and tangential maps versus peak locations in mean curvature maps. (a) Horizontal position, (b) vertical position.

When the horizontal (x) dimension cone peak locations from axial and tangential maps were plotted against mean curvature maps, the cone peaks appeared more nasally, though the trend for the tangential maps was much less obvious (FIG. 11a). The vertical (y) dimension cone peak locations from axial and tangential maps were also plotted against mean curvature maps (FIG. 11b). In this case, the axial maps deviated more from the mean curvature maps and tended to make the cone peaks appear more inferiorly located. In contrast, the tangential maps agreed with the mean curvature maps. The distance between the locations of the apparent cone peaks identified on axial vs mean curvature maps was 0.38±0.83 mm (P=0.026) on the horizontal axis, −0.23±0.39 mm (P=0.0046) on the vertical axis, and 0.90±0.45 mm in total. The distance between the locations of the apparent cone peaks identified on tangential vs mean curvature maps was 0.19±0.50 mm (P=0.062) on the horizontal axis, −0.00±0.18 mm (P=0.90) on the vertical axis, and 0.45±0.32 mm in total.

Comparison between the early and advanced keratoconus subgroups (Table 2) showed some expected differences. The cones were more convex in the advanced subgroup. However, this difference was not statistically significant, probably because of the small sample size. There were also no marked differences in the diameters, vertical, or horizontal peak positions.

Figure 12:
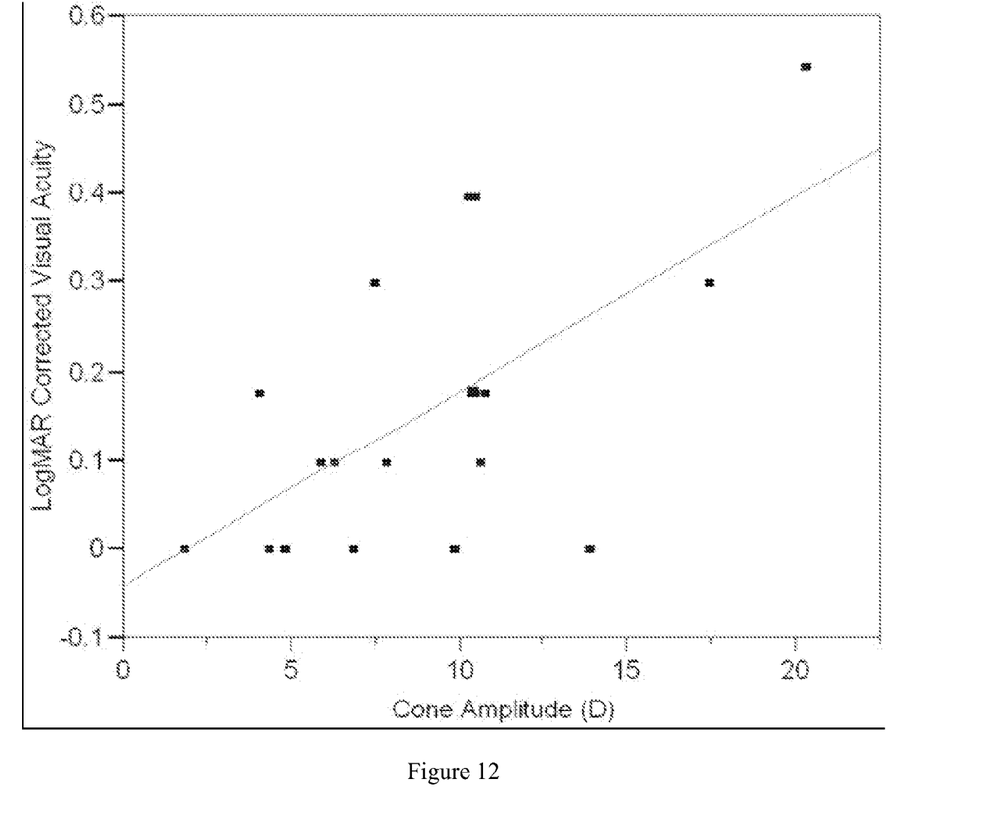
FIG. 12 LogMAR CVA plotted as a function of cone amplitude. Linear regression yielded intercept=−0.042, slope=0.022/diopter, $R^2$=0.39, and P=0.0044.

The amplitude of cone was significantly correlated with corrected visual acuity (CVA). Linear regression of the keratoconus dataset showed that each diopter increase in cone amplitude on mean curvature map was associated with a loss of 0.22 line in CVA ($R^2$=0.39, P=0.0044, FIG. 12). Some of the CVAs were obtained with spectacles and others with rigid gas permeable contact lens or soft contact lens. We were not able to ascertain the mode of correction because of limitations in the retrospective review of clinical chart notations. The correlation may have been even higher if best spectacle-OVA had been obtained in all cases.

In addition to fitting on mean curvature maps, we also tested Gaussian cone fitting on elevation maps. The elevation maps were relative to best-fit spheres or float maps. In our simulation series (FIGS. 4, 5, and 6), we placed an identical cone of 42 µm height and 3.6 mm FWHM diameter at various locations in combination with astigmatism. The recovered cone heights/widths were 3.9 µm/1.2 mm for the central keratoconus simulation, 16.7 µm/1.9 mm for the inferior keratoconus simulation, and 20.6 µm/1.9 mm for the PMD simulation. The average cross-correlation coefficients of Gaussian fitting on elevation maps were 0.68 in the keratoconus series and 0.64 in the PMD series.

Discussion

There are many theoretical advantages of using the mean curvature map to visualize and analyze ectatic diseases of the cornea such as keratoconus and PMD. First, it characterizes the local surfaces more completely by averaging curvatures along two principal axes. In contrast, axial and tangential powers only measure along the radial axis. Second, it captures the stretching of the surface in corneal ectasia. Imagine a flat drum surface. As it is inflated and becomes more convex, the surface area increases in proportion to the mean curvature value. This is the type of change that is quantified in the corneal mean curvature maps. Finally, it is insensitive to astigmatism.

Modern instruments, such as the Orbscan II corneal topography/tomography system, may be readily configured to automatically generate mean curvature maps. Here, the "keratometric mean power map" is on the basis of the mean curvature of the anterior corneal surface and is converted to the dioptric unit using the keratometric index of 1.3375. This instrument also computes the "total mean power map" on the basis of the mean curvatures of the anterior and posterior corneal topography plus the corneal thickness profile. It uses the refractive indices of air, cornea, and aqueous humor to obtain dioptric power.

Our study demonstrates that mean curvature mapping indeed captures the essence of keratoconus and PMD much better than axial and tangential power maps. Instead of many different patterns, all cases fit remarkably well to a simple Gaussian cone shape on the mean curvature map. While further enhancement might be obtained from the Gaussian fit by allowing different vertical and horizontal diameters, even with a single diameter the Gaussian function is an excellent approximation of the cone shape. The variations in individual cases are captured in two simple parameters: amplitude (D) and peak location (x, y). The amplitude relates well to the loss of CVA. The cone peak location appears to be the primary differentiator between keratoconus and PMD.

We performed many simulations before finding the ones that mimic actual keratoconus and PMD patterns on all three types of topographic representations shown here. The simulations taught us much about the interaction between the cone and overall corneal astigmatism. It was unexpectedly discovered that decentered cone seems to cause a flattening of the meridian upon which it is located. For clinicians experienced with astigmatic keratotomy, this may be similar to the effect of a relaxing incision. In the typical keratoconus case, the cone is slightly inferotemporal and produces an oblique astigmatism. Adding the oblique astigmatism to the preexisting with-the-rule astigmatism and a conic protrusion produces a pattern that closely mimics the typical keratoconus pattern (FIG. 5). In the typical PMD case, the cone is far inferior, leading to a predominantly against-the-rule astigmatism. Adding the cone produces the typical "butterfly" pattern on the axial and tangential maps (FIG. 6).

We used the keratometric index of 1.3375 to convert mean curvature to dioptric power. This follows the convention for keratometry and Placido-ring-based topography. We chose to follow convention so the clinician can use the same memorized range of normal values. For example, a value of 44 diopters would signify an approximate average cornea on both keratometry and keratometric mean curvature. However, one should use caution in interpreting any value or map on the basis of the keratometric index. Keratometric maps are on the basis of the assumption that anterior and posterior corneal surfaces have a fixed power ratio of around 1:10, and keratometric power represents the estimated total corneal power on the basis of the measurement of only the anterior surface. The assumption that anterior and posterior corneal power has a fixed relationship is not true for abnormal corneas with keratoconus or PMD. Therefore, the keratometric mean curvature is a poor measure of the spherical equivalent refractive power of abnormal corneas. Keratometric mean curvature should only be used to detect the shape abnormality rather than compute corneal refractive power. Corneal refractive power should be estimated using other methods. A recent study demonstrated "total optical power" by ray tracing of anterior and posterior corneal surfaces using physiologic refractive indexes [3]. This corresponds better to the refractive change after refractive surgery, compared with keratometric mean power map.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

TABLE 1

Cone Parameters of Keratoconus vs PMD Groups

|  | Diameter (mm) | Amplitude (D) | Vertical Peak Position* (mm) | Horizontal Peak Position[†] (mm) |
|---|---|---|---|---|
| Keratoconus (n = 19) | 2.94 ± 0.94 | 12.61 ± 6.01 | −1.10 ± 0.43 | −0.45 ± 0.33 |
| PMD (n = 8) | 4.47 ± 1.65 | 8.06 ± 2.68 | −1.94 ± 0.53 | −0.24 ± 0.43 |
| P value | .06 | .009 | .007 | .17 |

*Vertical peak position: "−" = inferior, "+" = superior.
[†]Horizontal peak position: "−" = temporal, "+" = nasal.

TABLE 2

Cone Characteristics of Early vs Advanced Keratoconus Subgroups

| | Diameter (mm) | Amplitude (D) | Vertical Peak Position* (mm) | Horizontal Peak Position[†] (mm) |
|---|---|---|---|---|
| Early keratoconus (n = 5) | 2.94 ± 0.75 | 10.65 ± 1.56 | −0.99 ± 0.38 | −0.48 ± 0.28 |
| Advanced keratoconus (n = 14) | 2.94 ± 0.98 | 13.31 ± 6.87 | −1.14 ± 0.46 | −0.44 ± 0.35 |
| P value of t test | 1 | .10 | .52 | .83 |

*Vertical peak position: "−" = inferior, "+" = superior.
[†]Horizontal peak position: "−" = temporal, "+" = nasal.

REFERENCES

[1] Wang J Y, Rice D A, Klyce S D. A new reconstruction algorithm for improvement of corneal topographical analysis. Refract Corneal Surg 1989;5:379-387;

[2] Tang M, Shekhar R, Huang D. Mean curvature mapping for the detection of corneal shape abnormality. IEEE Trans Med Imaging 2005;24:424-428;

[3] Sonego-Krone S, Lopez-Moreno G, Beaujon-Balbi O V, Arce C G, Schor P, Campos M. A direct method to measure the power of the central cornea after myopic laser in situ keratomileusis. Arch Ophthalmol 2004;122:159-166.

[4] Li Y, Shekhar R, Huang D. Corneal pachymetry mapping with high-speed optical coherence tomography. Ophthalmology 2006;113(5):792-9.

[5] Gonzalez-Meijome J M, Cervino A, Yebra-Pimentel E, Parafita M A. Central and peripheral corneal thickness measurement with Orbscan II and topographical ultrasound pachymetry. J Cataract Refract Surg 2003;29(1):125-32.

[6] Ucakhan O O, Ozkan M, Kanpolat A. Corneal thickness measurements in normal and keratoconic eyes: Pentacam comprehensive eye scanner versus noncontact specular microscopy and ultrasound pachymetry. J Cataract Refract Surg 2006;32(6):970-7.

What is claimed is:

1. A method of using a device that maps corneal thickness and anterior and posterior corneal topography to analyze cornea cone characteristics, said method comprises:
   measuring the corneal topography of a subject;
   computing and displaying a map of the cornea;
   fitting said map to a mathematical function having a cone-like shape; and determining and displaying the cone's location based on the fitting;
   wherein said measuring device uses software encoded on a computer readable media.

2. The method of claim 1, wherein said corneal map is a mean curvature map of the anterior surface of the cornea.

3. The method of claim 1, wherein said corneal map is a mean curvature map of the posterior surface of the cornea.

4. The method of claim 1, wherein said corneal map is an inverse normalized pachymetry map.

5. The method of claim 1, wherein said mathematical function is one selected from 4th-order zero-th period Zernike polynomials, a Alpha function, a Rayleigh function, a Cauchy function, or a Gaussian function.

6. The method of claim 5, wherein the Gaussian function is a two-dimensional Gaussian function comprising a single diameter for both the horizontal and vertical dimension.

7. The method of claim 5, wherein the two-dimensional Gaussian function comprises different vertical and horizontal diameters.

8. The method of claim 1 further comprises smoothing the map with a moving average window.

9. The method of claim 8, wherein the moving average window is a size from about 0.02 mm by 0.02 mm to about 2 mm by 2 mm.

10. The method of claim 8, wherein determining the cone's location comprises identifying the maximum mean curvature value from the smoothed map.

11. A computer implemented system for diagnosing corneal ectatic diseases, comprising:
   a device for measuring the surface map of a cornea; and
   a processing unit comprising a program for performing the method of claim 10.

12. A method of using a device that maps corneal thickness and anterior and posterior corneal topography to detect ectatic diseases of the cornea, said method comprises:
   measuring the corneal topography of a subject:
   providing a mean curvature map of the cornea;
   fitting said map to a mathematical function having a cone-like shape;
   determining and displaying the location of the cornea's cone based on the fitting; and
   comparing and displaying the location of the cone to a reference location of a healthy cornea,
   wherein if the location of the cone deviates from the reference location by a predetermined amount, a diseased state is detected, and wherein said measuring device uses software encoded on a computer readable media.

13. The method of claim 12, wherein said ecstatic disease is one selected from keratoconus and pellucid marginal degeneration.

14. The method of claim 12, wherein said mathematical function is one selected from 4th order Zernike polynomials, a Alpha function, a Rayleigh function, a Cauchy function, or a Gaussian function.

15. The method of claim 14, wherein said Gaussian function is a two-dimensional Gaussian function and has different horizontal and vertical diameters.

16. The method of claim 12, further comprising the step of smoothing the mean curvature maps with a moving average window.

17. The method of claim 16, wherein the moving average window has a size of from about 0.02 mm by 0.02 mm to about 2 mm by 2 mm.

18. The method of claim 12, further comprising determining the cone width by a search algorithm that maximized the cross-correlation coefficient between the mean curvature map and the Gaussian function.

19. The method of claim 12, wherein the width of the cone is equal to full-width-half maximum diameter of the Gaussian function.

20. The method of claim 12, further comprising the step of converting the curvature measurement of the mean curvature map from the natural inverse meter units into clioptric units.

* * * * *